(12) United States Patent
Xiao

(10) Patent No.: US 6,441,892 B2
(45) Date of Patent: Aug. 27, 2002

(54) COMPACT SPECTROFLUOROMETER

(75) Inventor: Ming Xiao, Fremont, CA (US)

(73) Assignee: Jobin Yvon, Inc., Edison, NJ (US)

( * ) Notice: Subject to any disclaimer, the term of this patent is extended or adjusted under 35 U.S.C. 154(b) by 0 days.

(21) Appl. No.: 09/813,325

(22) Filed: Mar. 19, 2001

Related U.S. Application Data

(63) Continuation of application No. 09/678,709, filed on Oct. 4, 2000, which is a continuation-in-part of application No. 09/443,392, filed on Nov. 19, 1999, now Pat. No. 6,323,944.

(51) Int. Cl.$^7$ .......................... G01N 21/64; G01N 21/27

(52) U.S. Cl. .......................... 356/73; 356/417; 356/419; 250/458.1

(58) Field of Search .................. 356/73, 416, 417, 356/419, 317, 318; 250/458.1, 459.1, 461.1, 461.2; 359/589, 590

(56) References Cited

U.S. PATENT DOCUMENTS 2,663,801 A * 12/1953 Slavin et al. ............... 356/417
4,937,457 A 6/1990 Mitchell
5,943,129 A 8/1999 Hoyt et al.

* cited by examiner

Primary Examiner—F. L. Evans
(74) Attorney, Agent, or Firm—Handal & Morofsky

(57) ABSTRACT

Spectrofluorometer employing a pair of linear variable spectral filters to produce a three dimensional data output is disclosed. A collimated white light source is used that first passes through a first linear variable spectral filter, then through a sample where fluorescence occurs, then the resultant light passes through a second linear variable spectral light filter that is oriented at ninety degrees from the first filter. The light is then detected by a CCD sensor for conversion into data. This arrangement provides a very simple, rugged and compact instrument that can be used almost anywhere, such as at the scene of a contamination accident.

8 Claims, 7 Drawing Sheets

COMPACT SPECTROFLUOROMETER

CROSS-REFERENCE TO A RELATED APPLICATION

This application is a continuation of commonly owned application Ser. No. 09/678,709 filed Oct. 4, 2000, the disclosure of which is hereby incorporated herein by reference thereto; which is a continuation-in-part of application Ser. No. 09/443,392, filed Nov. 19, 1999, now U.S. Pat. No. 6,323,944.

BACKGROUND OF THE INVENTION

Fluorescence instrumentation has been used for many years to identify unknown materials. Generally, the principle involved is that a material excited with light of a particular wavelength will emit light energy in the form of an emission spectrum whose amplitude profile, over the range of wavelengths emitted, constitutes a "fingerprint" which can give the identity and nature of the unknown material.

In the most demanding applications, a sample is excited with light of a single wavelength and the fluorescence emission spectrum is recorded. The wavelength of the excitation source is then advanced incrementally along the range of excitation wavelengths of interest, and the process repeated to record the fluorescence emission spectrum at the incremented wavelength. The process is continued until the entire range of excitation wavelengths of interest has been covered by the instrument. The result is a highly accurate, so-called three-dimensional fluorescence emission spectrum, showing excitation wavelengths, corresponding emission wavelengths and their amplitudes. Such instruments are of particular interest in scientific research where subtle variations in the characteristics of the spectrum may contain useful information to understand the effects of relatively subtle changes in the system. Typically, instruments of this sort have resolutions on the order of between 0.1 to 0.5 nm.

However, many applications have far less demanding requirements. For example, if one is merely interested in identifying the identity of a particular sample of material, far less resolution will suffice. Accordingly, a class of instruments having resolutions on the order of five to ten nanometers have seen widespread application in industry. Typical applications include the identification of samples of such material as blood, oil, pollutants and the like. Such instruments differ from other fluorescence instruments in that they are designed to perform measurements much more quickly, by measuring the fluorescence of a material over a range of wavelengths simultaneously.

Such a prior art system is illustrated in FIG. 1. Measurement of the fluorescence spectrum is achieved by having a system which comprises an excitation spectrograph 1 which is used to excite a sample 2, typically contained in. an elongated cuvette 3. The elongated cuvette 3 is excited by an elongated image of a spectrum extending from a low wavelength to a high wavelength.

This results in fluorescence emission by sample 2 in cuvette 3. The emission is received and collimated by a collimating concave mirror 4, which reflects the fluorescence emission to focusing concave mirror 5, which, in turn, focuses the emitted fluorescence light at a slit 6, through which the light which comprises the fluorescence emission passes to fall on the planar mirror 7. Planar mirror 7 reflects the light toward a spectrograph 8 formed by a concave aberration-corrected diffraction grating. Spectrograph 8 disperses a spectrum on a CCD detector 9 which in a single row of pixels can produce the complete emission spectrum of the excited material.

In a typical instrument of this type, a xenon source is dispersed as a spectrum placed over a cuvette along a vertical axis. Thus, the full spectrum will excite any homogeneous sample placed in the sample compartment of the cuvette. The resulting fluorescence emission is dispersed orthogonally over the active area of a rectangular CCD, or charge-coupled device, which is, essentially, a two-dimensional array of light detectors. The horizontal axis of the CCD records the emission spectra at different excitation wavelengths along the vertical axis, and gives the intensity for each wavelength. Thus, this instrument will produce, for each wavelength in the range of excitation wavelengths, the spectrum of emitted wavelengths. For example, if the system has a resolution of 5 nm, and covers a range of 100 nm, one could view the output as twenty different spectra.

The abiliby to complete a reading of the emission spectrum simultaneously opens up many possibilities for enhanced performance functions. For example, a cuvette may be fed by a high pressure liquid chromatography column, allowing the facile real-time generation of fluorescence emission spectra of the various materials in a sample being analyzed by the chromatography column.

While this system has many advantages over the prior art systems which measured a fluorescence spectrum one wavelength at a time, it still had a number of deficiencies. First, the volume required for the system is relatively large and precludes use of the system in a compact system. Moreover, the system comprises numerous expensive parts, and costs may be prohibitive for many applications. In addition, assembly of the system is unduly expensive requiring careful alignment of parts to ensure proper operation of the system. Similarly, the system is not as rugged as other systems, and is liable to become misaligned during use on account of shock and vibration. Finally, the system is limited to producing a fluorescence spectrum.

SUMMARY OF THE INVENTION

The invention, as claimed, is intended to provide a remedy. It solves the problems of large size, lack of ruggedness and cost by providing a simple instrument that can be implemented in a compact design. In accordance with the present invention, an excitation light source provides optical radiation over a range of wavelengths or spectra for illuminating a sample. The inventive instrument performs fluoresence analysis of samples, and comprises a light source emitting light into an illumination light path, and a first spectral filter in the illumination light path for transmitting light within a selected wavelength range. This defines a sample illumination light path. A second spectral filter is spaced from the first spectral filter forming a sample receiving space therebetween.

The illumination light path passes through the first spectral filter. The sample receiver and the second spectral filter lie in the light path, and the second spectral filter is displaced angularly relative to the first spectral filter. A sensing element in the resultant light path measures absorption spectra and fluorescence light. The first spectral filter and the second spectral filter have a characteristic which varies along an axis thereof. In accordance with the preferred embodiment of the invention, the variable characteristic is a variable bandpass wavelength in various filter regions of the spectral filter.

Also in accordance with the preferred embodiment, the second spectral filter is angularly displaced at a substantially othogonal angle.

The above described embodiment of the invention has the advantage of providing along a diagonal region of the CCD the absorption spectrum of the material sample under analysis.

In accordance with an alternative embodiment of the invention, a third spectral filter in the resultant light path is oriented in a direction, and position in a position which are substantially the same as the direction and position of the first spectral filter. This third filter serves the function of a blocking filter thereby preventing excitation light energy that has passed through a sample receiver from passing to the sensing element or CCD array.

BRIEF DESCRIPTION OF THE DRAWINGS

One way of carrying out the invention is described in detail below with reference to the drawings which illustrate one or more specific embodiments of the invention and in which like reference characters represent like elements.

DESCRIPTION OF THE PREFERRED EMBODIMENTS

Figure 1:
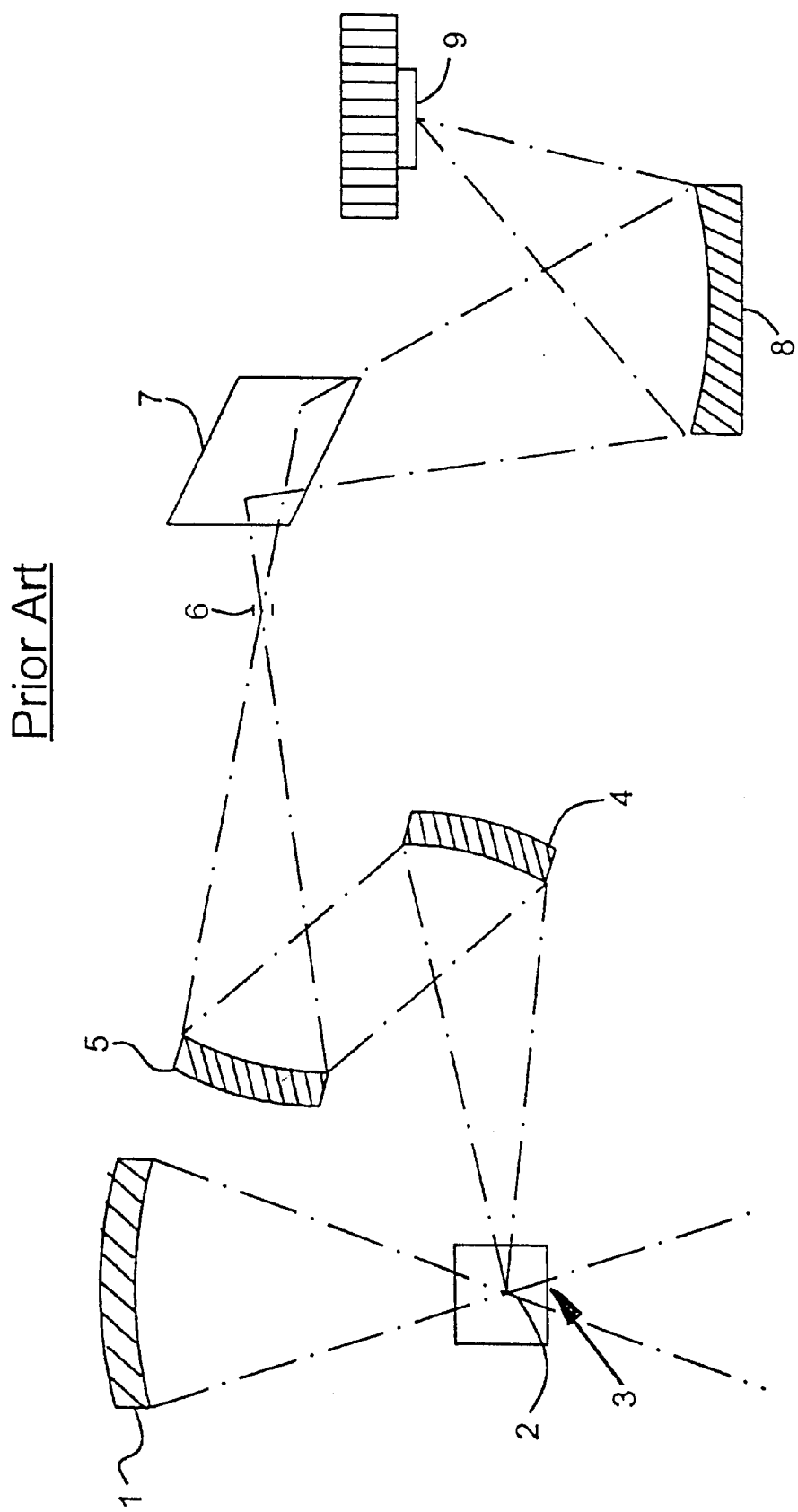
FIG. 1 is a schematic view of a typical prior art apparatus.
Figure 2:
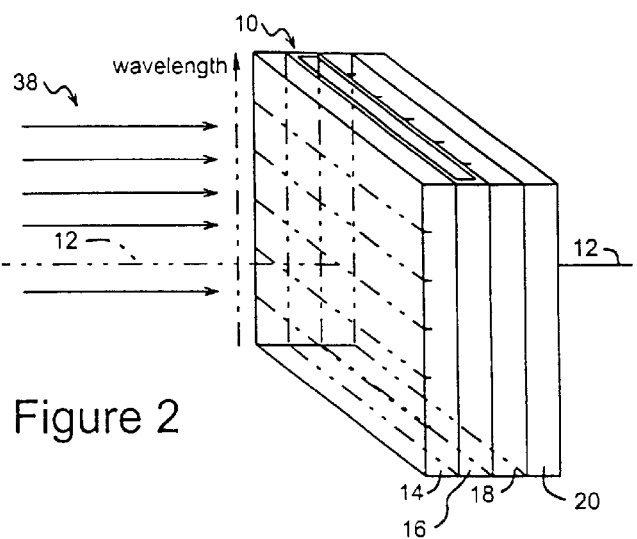
FIG. 2 is a schematic view of the present invention showing the compactness of the components.
Figure 3:
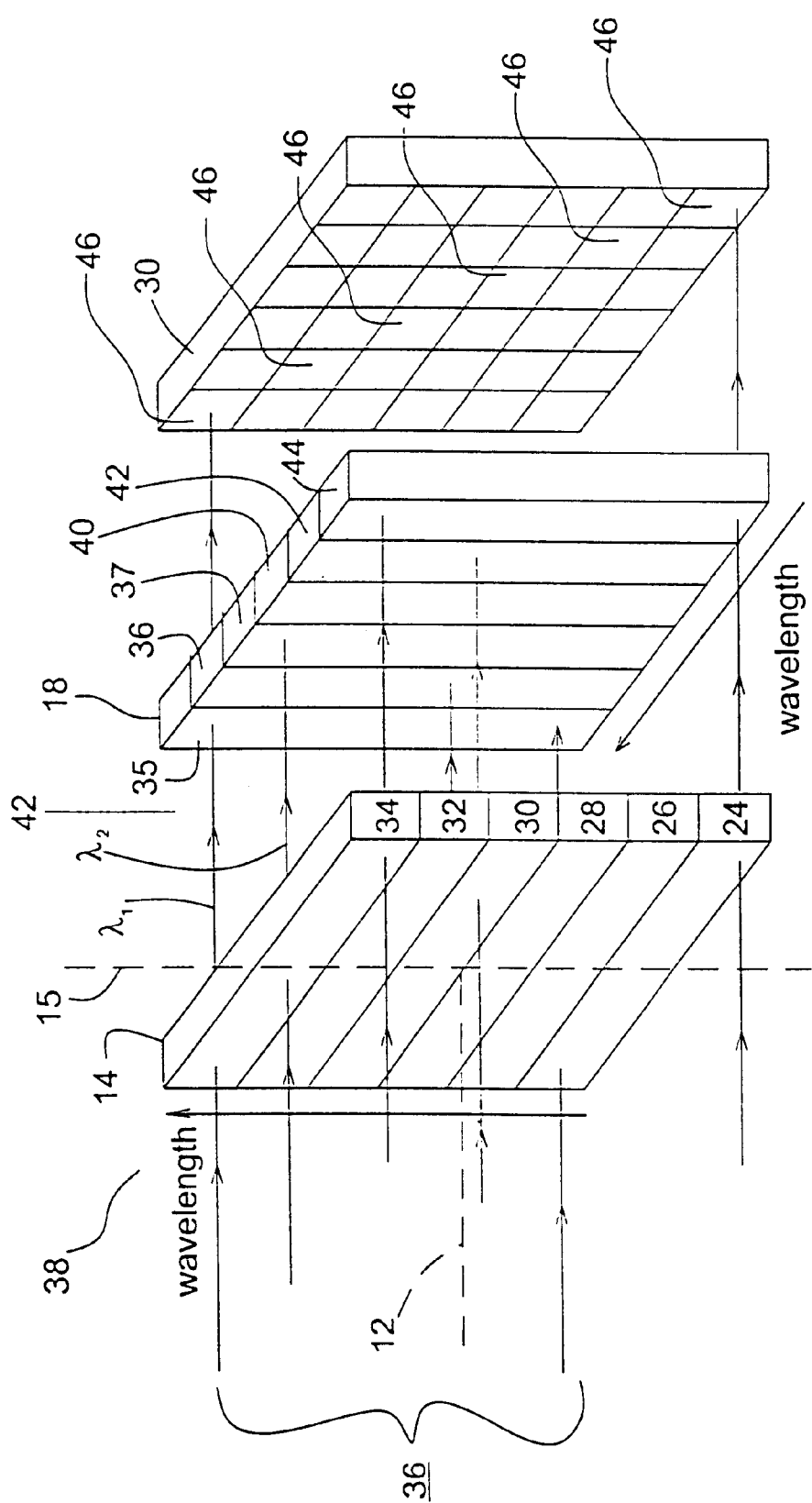
FIG. 3 is an exploded schematic view of the apparatus of the present invention showing a pair of linear variable spectral filter and a CCD type of sensing element.

Referring now to FIG. 2 and 3, major components of a Spectrofluorometer 10 are shown. Optical radiation traveling along an excitation light path 12 passes into a linear variable spectral filter 14.

Spectral filter 14 is a device which has bandpass wavelength characteristics which vary along its length. More particularly, at the bottom of filter 14, one wavelength would be passed in the region defined by the dashed lines. In the next filter region above that filter region like having a different wavelength will be passed, perhaps a wavelength which is 5 nm longer. This sort of device is made by advancing a mask having the width of one of the regions illustrated in dashed lines in the figure, from one discrete position to another and applying a different multilayer structure at each position to give the corresponding stripe of bandpass material the desired optical bandpass characteristic.

The manufacture of such a filter is known in the art and forms no part of the present invention. Such filters may be purchased on the open market and are available from, for example, Reynard Corporation under their catalog No. 4610. Such a filter has a spectral range of 400 to 700 nm. It is relatively small and compact, being 60 mm long, 25 mm wide and 5 mm thick. A typical spectrum length would be 44 mm, with dispersion varying between 0.12 and 0.17 mm/nm.

The linear variable spectral filters sold by this corporation tend to vary in their characteristics, with a spectrum length varying form 37 to 51 mm. matching of the filters used in the embodiment of FIG. 2 is desirable. Alternatively, a computer reading the output of the system may calibrate the software against a known source.

A sample receiver 16 is located between the first spectral filter 14 and a second linear variable spectral filter 18. Sample receiver 16 is a vessel which defines a volume for receiving a sample which is to be analyzed. It may be a rectangular solid made of glass, plastic or any suitable material. It may also be as simple as a glass slide with a smear of the sample, or even a solid film of the sample material, such as tissue, paper from a paper mill whose operation is being monitored, and so forth.

Such a sample may be a solution derived from a material being tested, blood, the output of an HPLC liquid chromatography column, or the like. If the output of an HPLC column is being monitored, the receiver 16 may have a liquid input port and a drain, and the dimensions of the receiver would be such that capillary action insures the presence of sample material throughout the excited regions of receiver 16. A charged-coupled discharge (CCD) sensing element 20 measures the relative position and intensity of light rays traveling along a resultant light path 12. See FIG. 3.

Figures 5, 6:
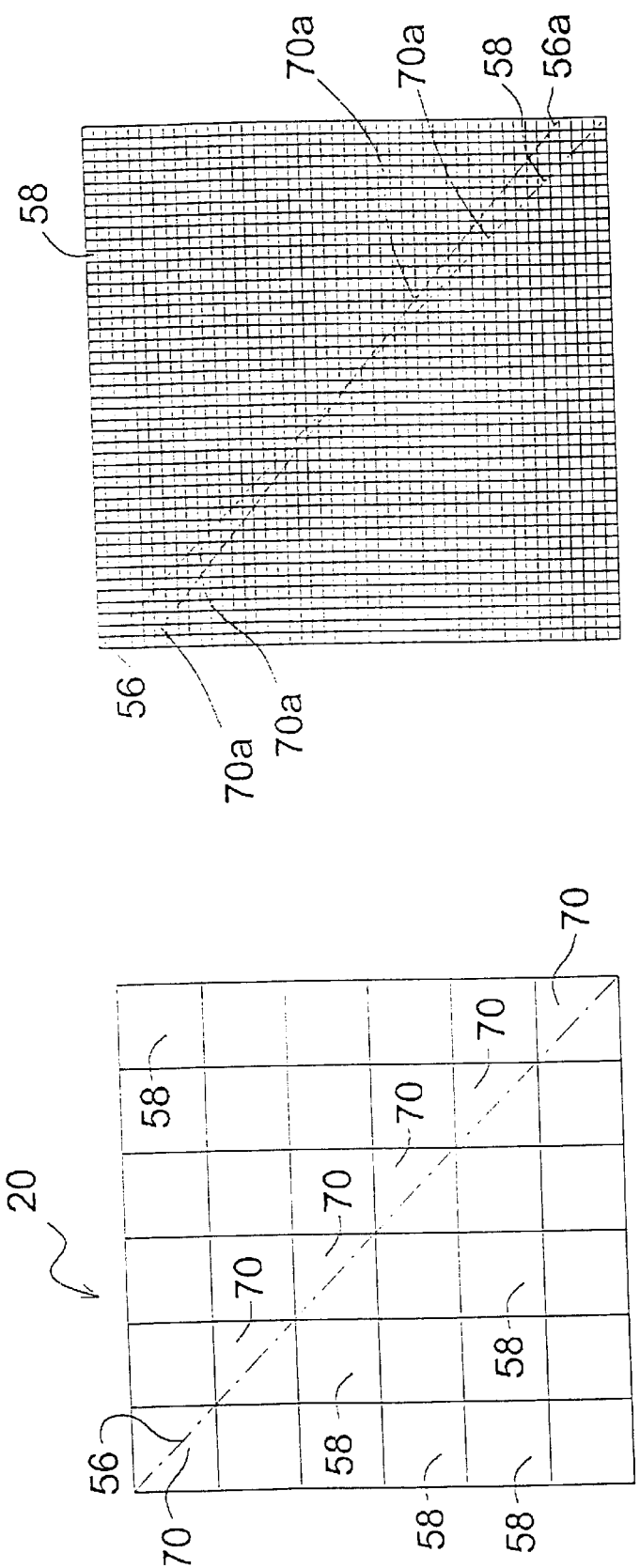
FIG. 5 is a schematic view of a CCD sensing element, as is employed in the embodiments illustrated in FIGS. 4 and 5.
FIG. 6 is a schematic view of a CCD sensing element, as is employed in the embodiments illustrated in FIGS. 4 and 5, illustrating the absorption spectrum position when filter elements are not matched in the system of the present invention.

Sensing element 20 is preferably a CCD type of sensor although other types can be used depending upon the type of excitation light used and the sample to be tested. In FIGS. 3 and 5, detector 20 is shown as a 36 element matrix detector. The small number of elements or pixels is merely for the convenience of illustration and the illustration of the principles of the invention. In a real device, the number of detectors easily ranges into the hundreds of thousands of elements, and, depending upon the performances desired and the nature of the software reading out the signal from the detector, the number of elements in detector 20 may range into the millions of pixels.

In principle, even film can be used in place of detector 20. An absorption spectrum and lamp profile (without sample) is shown as diagonal line 56 in FIG. 5. In connection with the preferred embodiment of the invention, a suitable sensing element is the CCD sold by Instruments SA on the Spectrum One. Each of these elements are described in detail below.

Referring back to FIG. 3, the borders defining the filter regions with different spectral characteristics in the first and second optical filters 14 and 18 are shown as dashed lines. First filter 14 is a linear variable spectral filter that changes its bandpass wavelength along the length or planar axis 15 of the filter. Wavelengths outside the desired transmission ranges are blocked by the respective filter regions.

In a preferred embodiment, the spectral range from 400 to 700 nm is oriented vertically, e.g., with shortest wavelength filter region 24 at the bottom, then longer wavelength filter region 26, still longer wavelength filter region 28, a filter region 30 which passes a range of wavelengths longer than those of filter region 28, a filter region 32 which passes a range of wavelengths longer than those of filter region 30, and the longest wavelength bandpass filter region than 34 at the top. While the invention has been implemented with a spectral filter having the aforementioned wavelength characteristics, other visible and non-visible bandpass characteristics can be used depending on the nature and characteristics of the sample to be tested.

The second optical filter 18 is substantially the same as the first optical filter 14 except that it is oriented in such a manner that its gradations are not in line with those of first filter 14. The strips defining the bandpass filter regions on filter 18 are preferably at ninety degrees to those of filter 14. The advantages of this relationship will now be described in connection with the operation of the inventive system.

A light source 36 which may comprise a xenon lamp whose output is collimated by a lens or reflector, or any other suitable optical components produces an excitation white light ray bundle 38, sometimes referred to as illumination light, that travels along excitation light path 12 with a wide range of wavelengths striking the surface of filter 14. As white light ray bundle 38 passes through filter 14, selected wavelengths are passed by each filter region, such that a wavelength "gradient" from short to long wavelengths is produced. This is referred to herein as a sample excitation light 42.

As sample excitation light 42 passes through second filter 18, only those wavelengths of light that are not blocked pass completely through the filter 18. Since filter 18 is oriented at a right angle to filter 14, most of sample excitation light 42 is blocked. By way of example, $\lambda_1$ passes through filter 14 and filter 18, while $\lambda_2$ passes through filter 14, but is blocked by filter 18. In this manner a diagonal spectral line 56 is transmitted onto sensing element 20. The theoretical center of this line it illustrated in FIG. 5 by phantom line 56. This intrinsic relationship between the two linear variable spectral filters provides for simplicity of design, ruggedness and compact size of the inventive spectrofluorometer 10.

Figure 4:
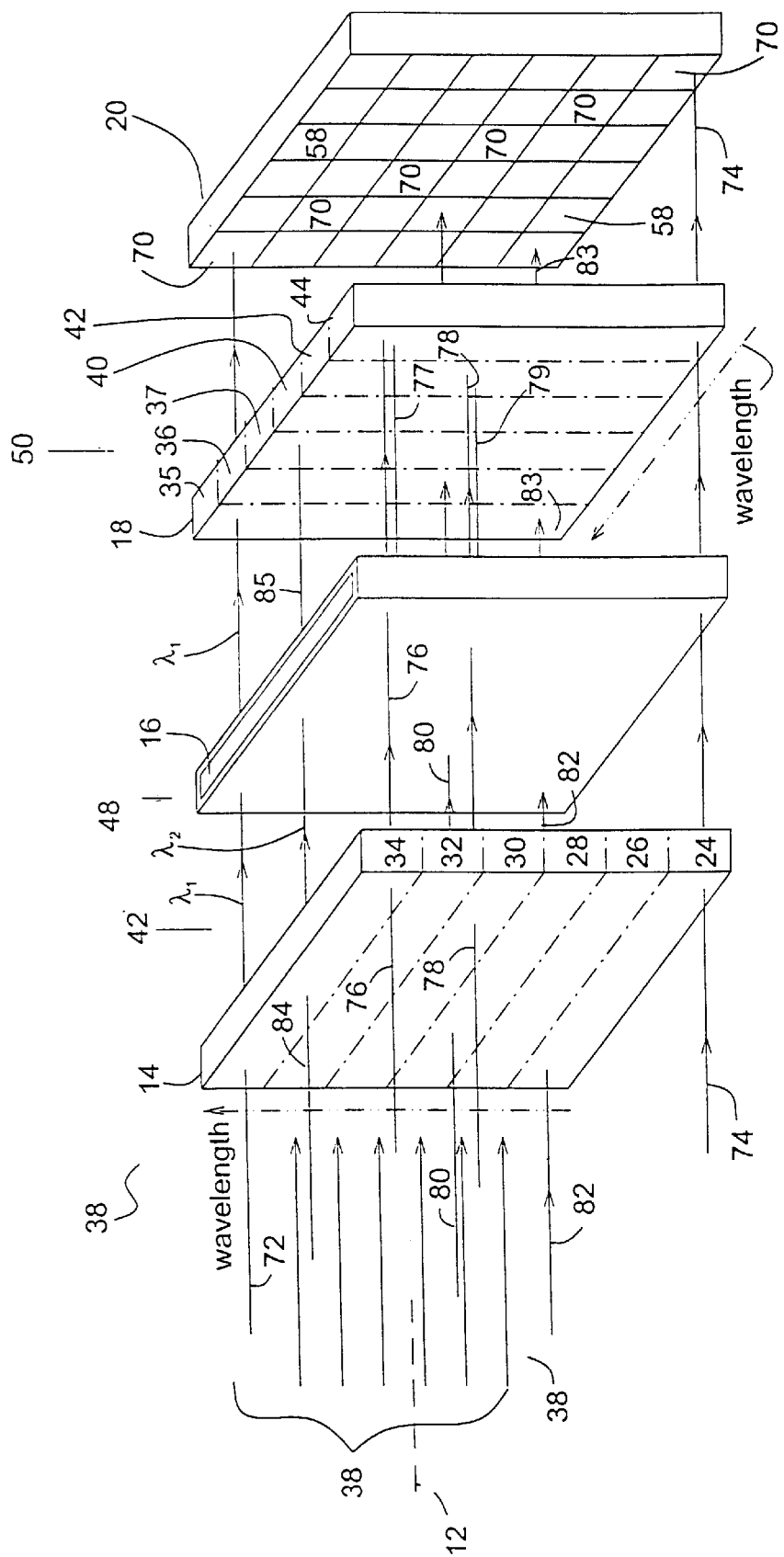
FIG. 4 is an exploded view similar to FIG. 3 including a cartridge containing a sample to be tested.

Referring now to FIG. 4, a sample receiver 16 is located between filter 14 and filter 18. Sample receiver 16 may be any of a number of conventional sample holding types or techniques. As sample excitation light passes through sample 44 some of the light energy is converted into fluorescence emissions. The physics of this conversion are well understood and generally involve the photon of excitation radiation raising the energy level of electrons in the excited atom to a higher energy level or shell. When the electron snaps back into its unexcited state, it emits a photon with an energy level lower that the exciting photon, thus resulting in the fluorescence having a wavelength longer than the excitation wavelength.

Some of the sample excitation light is "absorbed" by sample 44 and does not contribute to the emission. The net result is to increase the kinetic energy of the atoms of the sample, and thus raise the temperature of the sample.

A resultant light ray bundle 50, exiting sample receiver 16, comprises light rays which have exited filter 14 and fluoresence emissions from molecules that have been excited by light rays which have exited filter 14. Resultant light ray bundle 50 then passes into filter 18 where a selected wavelengths of both spectral light and fluorescent light are selectively blocked along the spectral gradient. The portions of light ray bundle 50 passing through to sensing element 20 constitutes the absorption spectrum 52 of the material being analyzed and appears along imaginary line 56 in FIG. 5. This can be used to identify sample 44.

As may be understood with reference to FIG. 4, filters 14 and 18 are substantially identical, but are positioned with their bandpass filter strip filter regions 24–34 and 35–44 oriented at right angles to each other. In accordance with the preferred embodiment of the invention, filter region 24 has the same bandpass characteristic as filter region 34. In accordance with the preferred embodiment of the invention, filter region 26 has the same bandpass characteristic as filter region 42. Filter region 28 has the same bandpass characteristic as filter region 40. Filter region 30 has the same bandpass characteristic as filter region 37. Filter region 32 has the same bandpass characteristic as filter region 36. Filter region 34 has the same bandpass characteristic as filter region 35.

Thus, the CCD elements 70, lying along line 56 in FIG. 5, are the only elements that will be illuminated by the white light ray bundle 38 coming from the excitation source. Moreover, because the fluorescence spectrum constitutes only wavelengths longer than the excitation wavelength, they will be blocked from reaching elements 70 by filter 18. Thus, only the absorption spectrum can be seen along imaginary line 56 to provide a first identification of the sample.

Likewise, because the fluorescence spectrum constitutes only wavelengths longer than the excitation wavelength, these longer wavelengths will be passed by filter 18 to those elements 58 of the CCD which lie below line 56 in FIG. 5. Thus, the elements 58 of the CCD which lie below line 56 in FIG. 5 produce the fluorescence emission spectra of the sample under analysis. The resultant fluorescence emission is used to identify sample 44.

Referring back to FIG. 4, the operation of the inventive system may be better understood. In particular, the output of the xenon lamp 36 constituting a broadband emission which is collimated into white light ray bundle 38 is caused to fall on filter 14, which outputs a plurality of stripes of light energy at different wavelengths. Because filters 14 and 18 are very thin, as is sample container 16, the output of filter 14 is effectively "imaged" on the sample in sample receiver 16. The output of sample container 16 is likewise effectively "imaged" on filter 18. Finally, in turn, the output of filter 18 is effectively "imaged" on the surface of CCD elements 58. The system works because all of the above thin elements are in contact with each other and CCD 20 to form the sandwich illustrated in FIG. 2.

As noted above, light ray 72, which is one of the light rays in white light bundle 38, because it is in the bandpass range of filter region 34 on filter 14, and, naturally, in the bandpass of optically identical filter region 35, will pass through both filters and fall on CCD 20, if it is not absorbed by the sample. The same is true for light ray 74, which is in the bandpass of filter regions 24 and 44.

Light rays 76 and 78 will, on the other hand, be blocked by filter 18, after being limited to the different bandpass of facing filter regions of filter 14. Moreover, any fluorescence emissions 77 and 79, corresponding respectively to light rays 76 and 78 will also be blocked by filter 18, as they must be longer in wavelength than the bandpass of the filter region of filter 14 that they pass through, and they fall on filter regions of filter 18 that are formed by filter regions that have shorter wavelength bandpass characteristics.

In contrast, light ray 80 has a wavelength corresponding to filter region 28, and thus more energy than light passed by filter region 36. Thus, it is physically possible that the sample will fluoresce with a lower energy and correspondingly longer wavelength light ray 81 that will pass through filter region 36 of filter 18. Likewise, highest energy light ray 82 which passes through filter region 26 and the sample may emit a low energy photon 83, which passes through filter region 35 and falls on the CCD detector.

Conversely, it is physically impossible that a sample will fluoresce with a higher energy and correspondingly shorter wavelength. Thus, a photon of light energy 84 passing through filter region 34 of filter 18 has the lowest energy in the system and the sample cannot emit a higher energy photon, and thus any light 85, whether transmitted or emitted by the sample will be blocked by filter region 38 which has a shorter bandpass wavelength than filter region 34. Thus, any such light will not reach the CCD detector.

Referring to FIG. 6, it can be seen that line 56, in the case where filter 14 is identical to filter 18, is a simple diagonal line. However, due to the nature of the manufacturing process use to produce filters 14 and 18, the layout of the various bandpass filter regions varies rather considerably. Accordingly, it is necessary to accommodate such variations if one cannot go to the trouble of trying to match identical filters very carefully.

Such variations may cause line 56 to shift to the position illustrated by reference number 56a in FIG. 6. Such variation occurs because the distance of oval which the series of spectral filters is dispersed is greater in filter 18 as compared to filter 14.

In the case of such variations, it is merely necessary to calibrate the software to the pattern on CCD 20. This can be done by determining the presence of the absorption spectrum and then mathematically adjusting the position of the fluorescence spectrum accordingly. This is done on the basis that the opposite ends of the absorption spectrum represent the horizontal and vertical limits of the fluorescence spectrum. Such determination can most easily be made without having a sample in the inventive fluorescence instrument 10.

As is alluded to above, filters 14 and 18 are made by depositing stripes of material which form bandpass filters on a substrate. As is also alluded to above, maximizing the thinness of instrument 10 will also maximize performance. More precisely, improved performance can be obtained by minimizing the distance between the active filter layer of filters 14 and 18 as well as minimizing the distance between the active layer of filter 18 and the sensitive face of detector 20. Thus, exceedingly thin substrates may be used to optimize the performance of the instrument.

Figure 7:
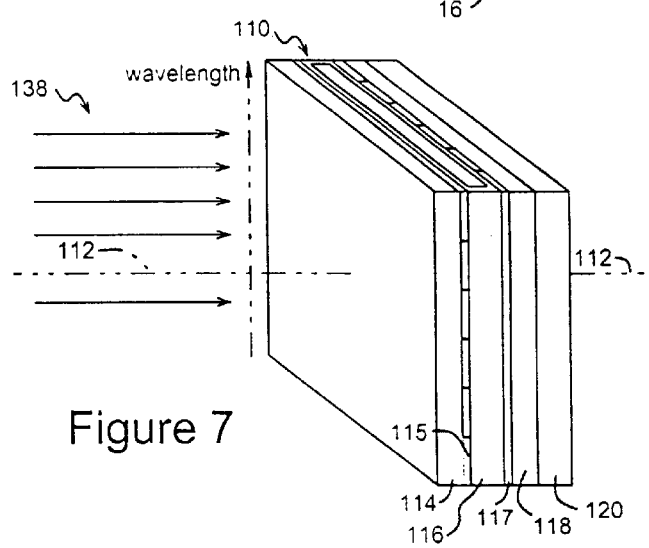
FIG. 7 is a perspective view of an alternative embodiment of the present invention.

Yet another approach is illustrated in FIG. 7. In FIG. 7 the convention of labeling parts with identical or analogous functions with numbers which vary by multiples of 100 has been followed.

In FIG. 7, the inventive Spectrofluorometer 110 is excited by excitation light 138 along path 112. Excitation light 138 first falls on filter 114, causing it to pass through the active layer 115 of filter 114 on the far side of filter 114. Light 138 then passes through the sample in receiver or carrier 116. Light 138 then passes through the active layer 117 of filter 116. Active layers 115 and 117 are formed on the substrates of their respective filters. Such substrates may be glass, plastic or any other suitable material. After passing through active layer 117, light 138 passes through the substrate of filter 116 and on to the sensitive face of detector 120, from which it is sent to a computer or other suitable device for interpreting and displaying the output of the detector.

Figure 8:
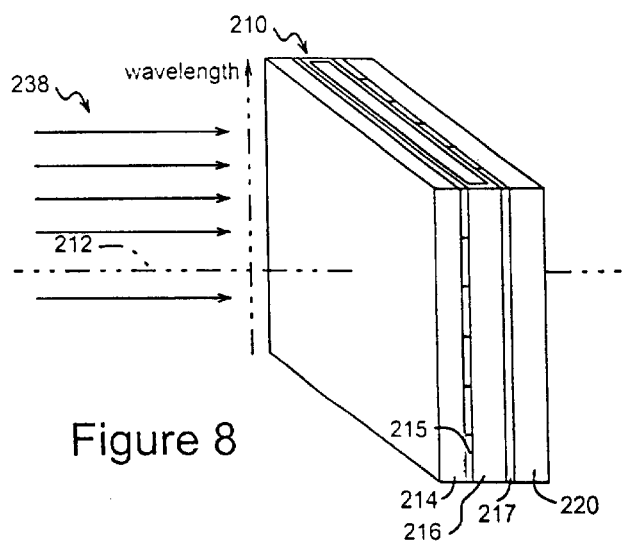
FIG. 8 is a perspective view of an alternative embodiment of the inventive Spectrofluorometer incorporating a further improvement.

Yet another approach is shown in FIG. 8. Here Spectrofluorometer 220 is excited by excitation light 238 along path 212. Excitation light 238 first falls on filter 214, causing it to pass through the active layer 215 of filter 214 on the far side of filter 214. Light 238 then passes through the sample in receiver or carrier 216. Light 238 then passes through the active filter layer 217, which is disposed and manufactured onto the output face of carrier or receiver 216. Alternatively, active filter layer 217 may be disposed on and manufactured onto the input face of detector 220. After passing through active layer 217, light 238 passes onto the sensitive face of detector 220, from which it is sent to a computer or other suitable device for interpreting and displaying the output of the detector.

As will the apparent from FIG. 8, the distance between filtered light exiting the first active bandpass layer in the inventive system 220, and the sensitive face of detector 220 is minimized in FIG. 8. Accordingly, light which is not traveling perpendicular to the faces of the filters, then, accordingly, is dispersed in itself, travels over a minimized path length and, accordingly, the dispersion is minimized, thus eliminating the need for the focusing optics, which are so important in prior art systems.

Figure 9:
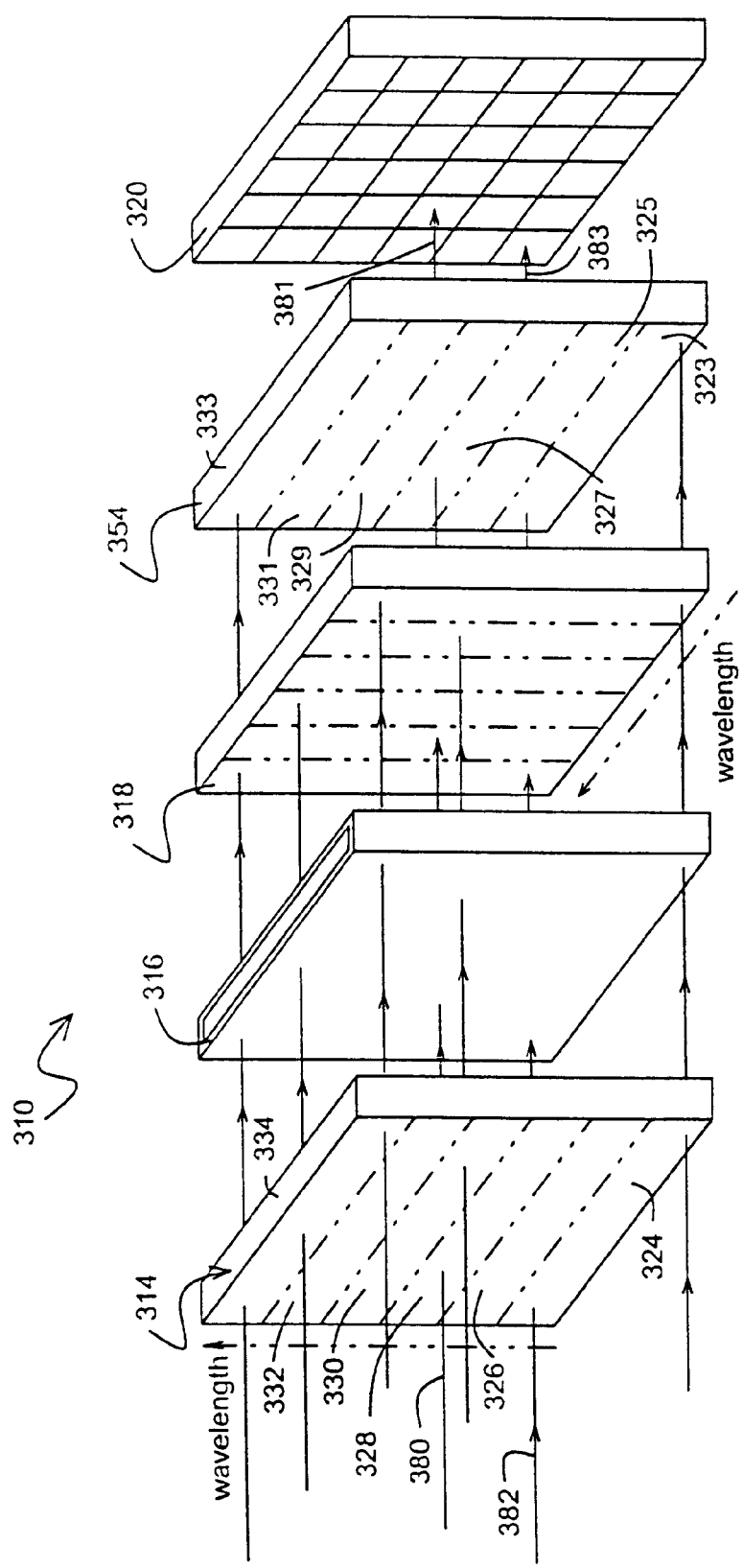
FIG. 9 is a view similar to FIG. 4 of an alternative embodiment of the invention including an excitation light blocking filter.

Referring to FIG. 9, a spectrofluorometer 310 having the feature of being able to block the excitation wavelength of the system is illustrated. This is desirable because the amplitude of the excitation wavelength will often spread and overload the detector receiving light from adjacent filter regions. The instrument illustrated in FIG. 9, operates in the same manner as the instrument illustrated in FIG. 4, except for this additional feature.

In particular, it has a filter 314, a sample carrier 316, a filter 318, and a detector 320. The characteristics of all of these systems is the same as the instrument illustrated in FIG. 4. However, it also has a spectral band reject filter 354, which is aligned, filter region by filter region, to substantially identically opposite filter 314.

More particularly, in accordance with the preferred embodiment of the invention, filter region 323 has a band reject characteristic with the same wavelength range as the wavelength range of the bandpass characteristic of filter region 324. In accordance with the preferred embodiment of the invention, filter region 325 has a band reject characteristic with the same wavelength range as the wavelength range of the bandpass characteristic of filter region 326. Filter region 327 has a band reject characteristic with the same wavelength range as the wavelength range of the bandpass characteristic of filter region 328. Filter region 329 has a band reject characteristic with the same wavelength range as the wavelength range of the bandpass characteristic of filter region 330. Filter region 331 has a band reject characteristic with the same wavelength range as the wavelength range of the bandpass characteristic of filter region 332. Filter region 333 has a band reject characteristic with the same wavelength range as the wavelength range of the bandpass characteristic of filter region 334. The blocking of excitation wavelengths is thus assured and the detection of low amplitude fluorescence signals is enhanced.

Figure 10:
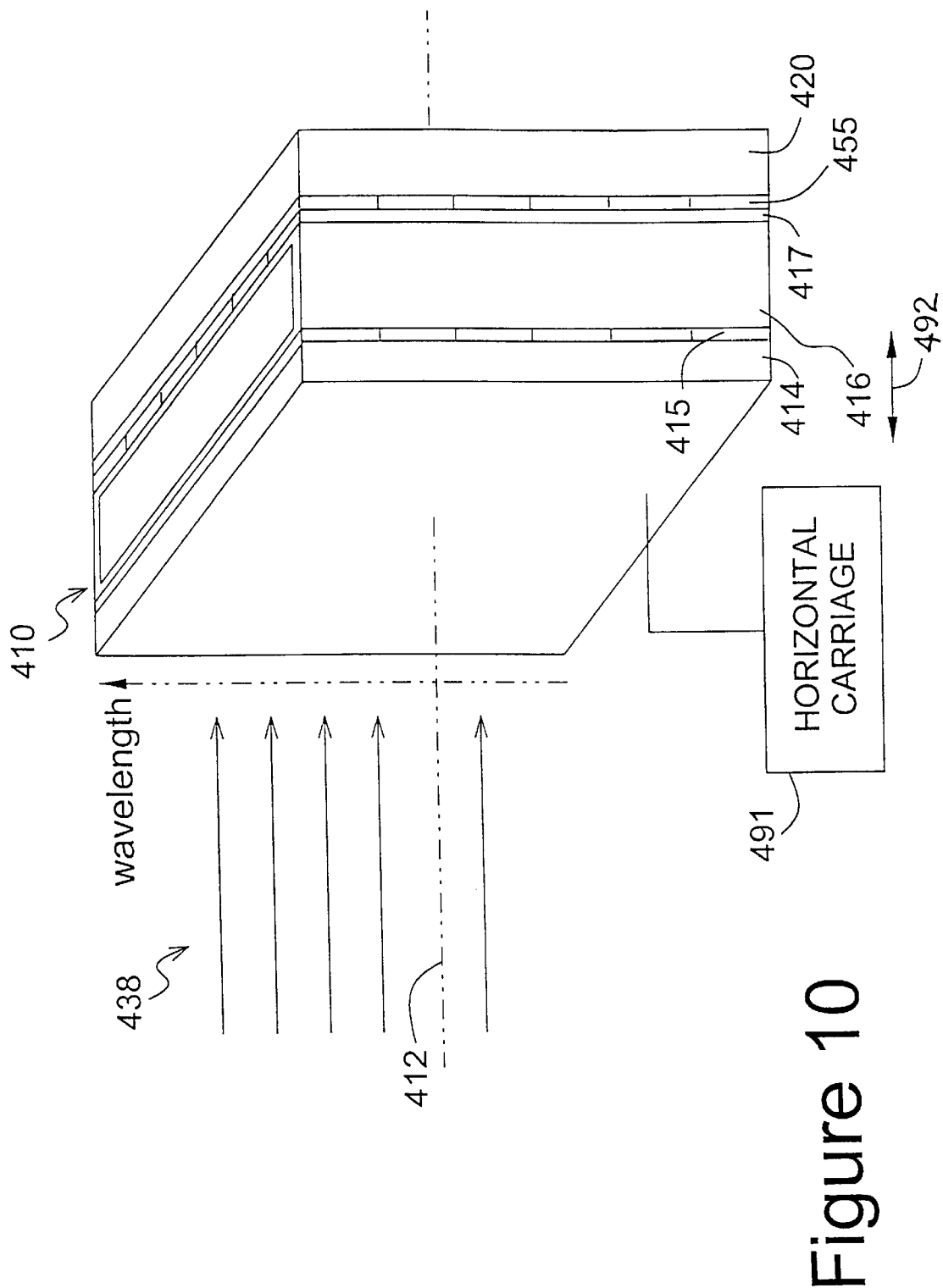
FIG. 10 is a perspective view of an embodiment of the invention similar to that illustrated in FIGS. 9 and incorporating minimized light paths.

Another embodiment, shown in FIG. 10, is substantially identical to the instrument of FIG. 9, except that active filter layer 415 of spectrofluorometer 410 is deposited on the substrate of filter 414 on the side of filter 414 closer to the sample to be analyzed, and active filter layers 417 and 455 are deposited on the sensitive face of CCD 420 (on the side of filter 414 closer to the sample to be analyzed). This is done in order to minimize the lengths of paths of dispersion, and thus minimize dispersion and optimize the operation of the instrument. Active filter layer 455 is identical to filter 354 in FIG. 9.

Active filter layer 415 is made by advancing a mask along the substrate of filter 414 having the width of one of the regions illustrated in the figure, from one region to the next and applying the appropriate multilayer structure at each position to give the desired stripe of bandpass material the desired optical bandpass characteristic. Active filter layer 417 is made by performing the same process, first applying to the sensitive face of CCD 420 the same series of different multilayer structures at their respective positions to give the corresponding stripes of filter layer 417 the desired optical bandpass characteristic. CCD 420 is then rotated in the plane of its sensitive face by 90 degrees.

Active filter layer 455 is made by advancing, along the rotated substrate of CCD 420, a mask having the width of one of the regions illustrated in FIG. 10, from one region to the next and applying the appropriate multilayer structure at each position to give the desired stripe of band reject material the desired optical band reject characteristic. When the process is completed, the result is a filter layer 455 is the band reject analog of bandpass filter layer 415.

In accordance with the present invention, it is may be desirable, in order to accommodate the insertion of different sample receivers or carriers 416, to vary the distance between filter layers 415 and 417. This may be achieved by mounting filter 414 on a horizontally moveable table 491 or other mechanism. This enables movement in the directions indicated by arrow 492.

The positions of layers 417 and 455 may be reversed by reversing their order of deposit. Likewise, the active filter layers may be deposited on the sample receiver or carrier to provide sample carriers that have filter patterns which may embody the operation of any of the systems described above. Such sample carriers may be specialized to optimize the analysis of certain classes of analysis tasks, such as blood work, where it may be desirable to perform special filtering, to block, transmit or study certain portions of the spectrum. One or more filter layers may be placed on either or both sides of the sample carrier.

While an illustrative embodiment of the invention has been described, it is, of course, understood that various modifications of the invention may be made by those of ordinary skill in the art without departing from the spirit and scope of the invention which is limited and defined only by the appended claims.

What is claimed is:

1. An instrument for measuring the wavelength characteristics of light output from a material in response to a light input, comprising:

(a) a light source for producing input light;

(b) a first filter, said first filter defining a first active area, said first filter being positioned to receive said input light from said source, said first filter having a characteristic that varies from position to position along said first active area, said first filter transmitting a portion of said input light through said first filter as first filtered light;

(c) a second filter, said second filter defining a second active area, said second filter being positioned to receive said first filtered light from said first filter, said second filter being positioned in facing spaced relationship to said first filter to define a space for the placement of a sample to be analyzed, said second filter having a characteristic that varies from position to position along said second active area, said second filter transmitting a portion of said input first filtered light through said second filter as second filtered light, at least some of the facing portions of said second filter facing said first filter having a transmissive characteristic different from that of the facing portion of said first filter;

(d) a detector for detecting said second filtered light, said detector being a two dimensional array;

(e) a third filter, said third filter defining a third active area, said third filter being positioned to receive said second filtered light from said second filter, said third filter having a characteristic being a band reject analog of the bandpass characteristic of said first filter, said third filter blocking said first filtered light and transmitting at least a portion of said input second filtered light through said third filter as third filtered light, said third filtered light passing on to said detector, whereby excitation wavelengths do not overload the detector and hinder the detection of fluorescence emissions;

wherein said first and second filters have a bandpass characteristic which varies from position to position to allow the measurement of an emission spectrum; and wherein said first and second filters each comprise a series of strips with different bandpass characteristics, and are angularly positioned with respect to each other.

2. An instrument as in claim 1, wherein said first and second filters are positioned at substantially a right angle with respect to each other.

3. An instrument as in claim 1, wherein said first and second filters are positioned with their active surfaces facing toward each other.

4. An instrument for spectro-fluoresence analysis of samples, said instrument comprising:

a light source emitting light along an illumination light path;

a first spectral filter in said illumination light path; said light source, and transmitting light within a selected wavelength range;

a second spectral filter, said second spectral filter spaced from said first spectral filter forming a sample receiver there between, said illumination light path passing through said first spectral filter, said sample receiver and said second spectral filter, said second spectral filter being displaced angularly relative to said first spectral filter;

a sensing element in said resultant light path for measuring absorption spectra and fluorescence light; and a third spectral filter in said resultant light path being oriented similarly to said first spectral filter and being a blocking filter with a wavelength characteristic that prevents illumination light that has passed through said sample receiver from passing through said third spectral filter.

5. An instrument according to claim 4, wherein said first spectral filter, said second spectral filter and said third spectral filter each include a variable characteristic along an axis defined by at least two of said first spectral filter, said second spectral filter and said third spectral filter.

6. An instrument according to claim 5, wherein said variable characteristic includes different bandpass regions across said axis.

7. An instrument according to claim 6, wherein said second spectral filter is angularly displaced at an approximately orthogonal angle.

8. An instrument according to claim 4, wherein said sensing element is a CCD.

* * * * *